United States Patent
Pretz et al.

(10) Patent No.: US 10,688,477 B2
(45) Date of Patent: Jun. 23, 2020

(54) PROCESS FOR REACTING OXYGEN CARRYING REGENERATED CATALYST PRIOR TO USE IN A FLUIDIZED BED REACTOR

(71) Applicant: Dow Global Technologies LLC, Midland, MI (US)

(72) Inventors: Matthew T. Pretz, Freeport, TX (US); Liwei Li, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/094,582

(22) PCT Filed: May 5, 2017

(86) PCT No.: PCT/US2017/030582
§ 371 (c)(1),
(2) Date: Oct. 18, 2018

(87) PCT Pub. No.: WO2017/196586
PCT Pub. Date: Nov. 16, 2017

(65) Prior Publication Data
US 2019/0099745 A1    Apr. 4, 2019

Related U.S. Application Data

(60) Provisional application No. 62/333,334, filed on May 9, 2016.

(51) Int. Cl.
*B01J 23/96*     (2006.01)
*C10G 11/18*     (2006.01)
(Continued)

(52) U.S. Cl.
CPC ............... *B01J 23/96* (2013.01); *B01J 8/003* (2013.01); *B01J 8/0015* (2013.01); *B01J 8/0025* (2013.01);
(Continued)

(58) Field of Classification Search
CPC ... B01J 23/96; B01J 38/10; B01J 38/04; B01J 38/02; B01J 23/62; B01J 8/18;
(Continued)

(56) References Cited

U.S. PATENT DOCUMENTS 4,260,475 A * 4/1981 Scott ..................... B01J 21/20
208/113
4,719,189 A    1/1988 Krishnamurthy
(Continued)

FOREIGN PATENT DOCUMENTS

GB    1547731 A    6/1979
WO    9523123 A1   8/1995
(Continued)

OTHER PUBLICATIONS

International Search Report and Written Opinion pertaining to PCT/US2017/030582, dated Aug. 9, 2017.
(Continued)

*Primary Examiner* — Ali Z Fadhel
(74) *Attorney, Agent, or Firm* — Dinsmore & Shohl LLP

(57) ABSTRACT

A process to react an oxygen containing regenerated catalyst stream prior to use in a fluidized bed reactor comprising providing a regenerated catalyst stream which comprises at least 0.001 wt % oxygen; reacting the regenerated catalyst stream with a fuel source thereby forming oxides and reducing the amount of oxygen in the regenerated catalyst stream to produce a usable regenerated catalyst stream; and injecting the usable regenerated catalyst stream into a hydrocarbon fluidized bed reactor is provided.

13 Claims, 1 Drawing Sheet

(51) Int. Cl.

| | | |
|---|---|---|
| *B01J 38/18* | (2006.01) | |
| *B01J 8/00* | (2006.01) | |
| *B01J 8/18* | (2006.01) | |
| *B01J 8/34* | (2006.01) | |
| *B01J 8/26* | (2006.01) | |
| *B01J 23/62* | (2006.01) | |
| *B01J 38/02* | (2006.01) | |
| *B01J 38/04* | (2006.01) | |
| *B01J 38/10* | (2006.01) | |
| *C07C 5/333* | (2006.01) | |
| *B01J 38/30* | (2006.01) | |

(52) U.S. Cl.
CPC ........... *B01J 8/0055* (2013.01); *B01J 8/0065* (2013.01); *B01J 8/18* (2013.01); *B01J 8/1818* (2013.01); *B01J 8/26* (2013.01); *B01J 8/34* (2013.01); *B01J 23/62* (2013.01); *B01J 38/02* (2013.01); *B01J 38/04* (2013.01); *B01J 38/10* (2013.01); *B01J 38/18* (2013.01); *C07C 5/3332* (2013.01); *C10G 11/182* (2013.01); *B01J 38/30* (2013.01); *B01J 2208/00663* (2013.01); *B01J 2208/00752* (2013.01); *C10G 2300/4093* (2013.01); *C10G 2300/703* (2013.01)

(58) Field of Classification Search
CPC ............ B01J 8/0015; B01J 2208/00752; B01J 2208/00663; B01J 38/30; B01J 8/0065; B01J 8/0055; B01J 8/003; B01J 8/0025; B01J 8/34; B01J 8/26; B01J 8/1818; B01J 38/18; C07C 5/3332; C10G 2300/703; C10G 2300/4093; C10G 11/182

See application file for complete search history.

(56) References Cited

U.S. PATENT DOCUMENTS

| | | | |
|---|---|---|---|
| 4,912,273 A | 3/1990 | Harandi et al. | |
| 5,011,592 A * | 4/1991 | Owen | C10G 11/182 208/113 |
| 5,019,353 A | 5/1991 | Harandi et al. | |
| 6,392,113 B1 | 5/2002 | Gartside | |
| 8,669,406 B2 * | 3/2014 | Pretz | C07C 5/3332 585/440 |
| 2008/0004173 A1 * | 1/2008 | Miura | B01J 23/002 502/53 |
| 2010/0152516 A1 | 6/2010 | Naunheimer et al. | |
| 2011/0257451 A1 | 10/2011 | Thorman et al. | |
| 2012/0123177 A1 | 5/2012 | Pretz et al. | |
| 2017/0333889 A1 * | 11/2017 | Clancy-Jundt | B01J 38/18 |

FOREIGN PATENT DOCUMENTS

| | | |
|---|---|---|
| WO | 2005077867 A2 | 8/2005 |
| WO | 2011121613 A1 | 10/2011 |
| WO | 2013009820 A1 | 1/2013 |
| WO | 2016069918 A1 | 5/2016 |
| WO | 2016160273 A1 | 10/2016 |
| WO | 2017196602 A1 | 11/2017 |

OTHER PUBLICATIONS

Examination Report pertaining to G.C.C. Patent Application No. 2017-33315, dated Apr. 16, 2019.
Examination Report pertaining to corresponding G.C.C. Patent Application No. 2017-33315, dated Nov. 20, 2019.

* cited by examiner

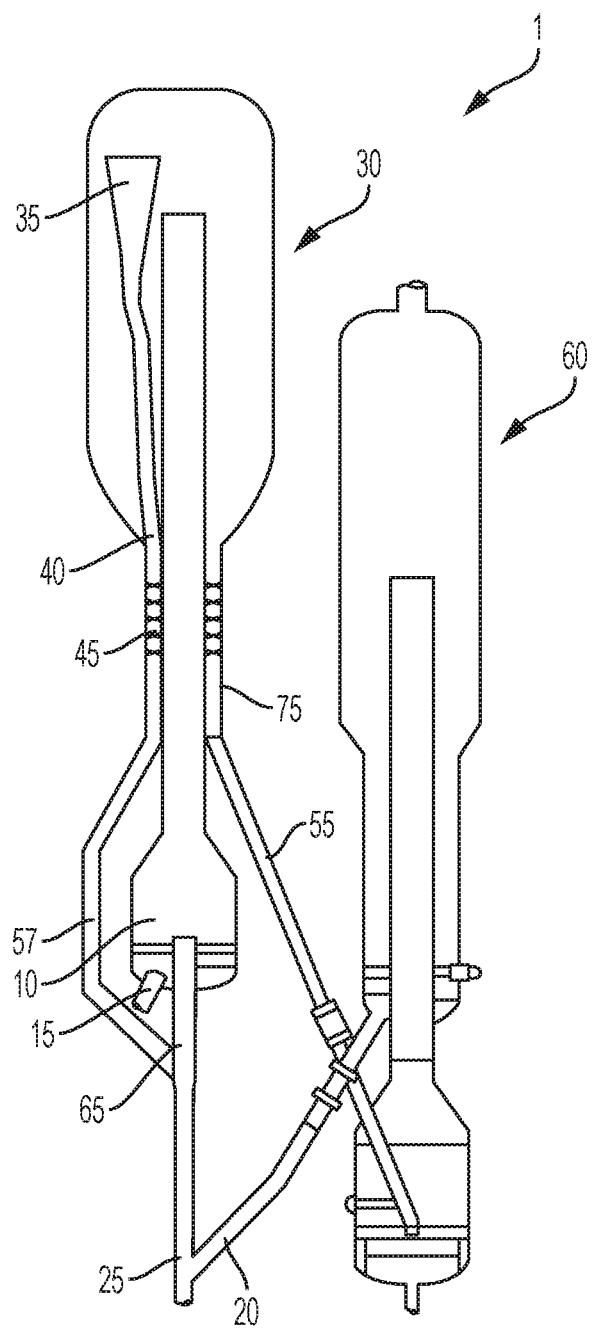

PROCESS FOR REACTING OXYGEN CARRYING REGENERATED CATALYST PRIOR TO USE IN A FLUIDIZED BED REACTOR

CROSS-REFERENCE TO RELATED APPLICATIONS

This application claims priority to U.S. Provisional Application, 62/333,334, filed May 9, 2016, which is incorporated herein by reference in its entirety.

FIELD OF INVENTION

The instant invention relates to a process for reacting oxygen out of regenerated catalyst prior to use in a fluidized bed reactor.

BACKGROUND OF THE INVENTION

Fluidized bed reactors are used in a number of industrial chemical processes, such as hydrocarbon dehydrogenation, fluidized catalytic cracking (FCC) and methanol to olefins (MTO).

In processes for hydrocarbon dehydrogenation to produce olefins, the art has taught that regenerated catalyst must be stripped to minimize oxygen in the regenerated catalyst stream prior to injection into the dehydrogenation reactor. For example, the regenerated catalyst stream may be stripped with a nitrogen stream.

The inclusion of an oxygen stripper increases the capital investment of a hydrocarbon dehydrogenation process, increases the operating cost due to nitrogen consumption and increases the complexity of unit operation. Therefore, one might consider eliminating the unit operation. This gives rise to the problem of oxygen being transferred to the dehydrogenation reactor and degrading valuable feedstock to less valuable products.

Therefore, a process for minimizing the oxygen amount arriving in the fluidized bed reactor along with the regenerated catalyst would be useful.

SUMMARY OF THE INVENTION

In one embodiment, the disclosure provides a process to react an oxygen containing regenerated catalyst stream prior to use in a fluidized bed reactor comprising providing a regenerated catalyst stream which comprises at least 0.001 wt % oxygen; reacting the regenerated catalyst stream with a fuel source such as methane, ethane, ethylene, propane, propylene, hydrogen, or coke thereby forming oxides and reducing the amount of oxygen in the regenerated catalyst stream to produce a usable regenerated catalyst stream; and injecting the usable regenerated catalyst stream into a hydrocarbon fluidized bed reactor. In one embodiment, the amount of fuel would be at least the stoichiometric amount required to react out the available oxygen.

BRIEF DESCRIPTION OF THE DRAWINGS

For the purpose of illustrating the invention, there is shown in the drawings a form that is exemplary; it being understood, however, that this invention is not limited to the precise arrangements and instrumentalities shown.

FIG. 1 is a schematic illustrating one equipment configuration for operating an embodiment of the inventive process.

DETAILED DESCRIPTION OF THE INVENTION

In a first embodiment, the disclosure provides a process to react an oxygen containing regenerated catalyst stream prior to use in a fluidized bed reactor comprising providing a regenerated catalyst stream which comprises at least 0.001 wt % oxygen based on the total weight of the regenerated catalyst stream; reacting the regenerated catalyst stream with a fuel source thereby forming oxides and reducing the amount of oxygen in the regenerated catalyst stream to produce a usable regenerated catalyst stream; and injecting the usable regenerated catalyst stream into a hydrocarbon fluidized bed reactor. All individual values and subranges from at least 0.001 wt % oxygen are included and disclosed herein; for example, the amount of oxygen in the regenerated catalyst stream may be from at least 0.001, 0.01, 0.1 or 0.5 wt %. All individual values and subranges from at least 0.001 wt % are included and disclosed herein. In specific embodiments, the amount of oxygen in the regenerated catalyst stream may range from 0.001 to 0.5 wt %, or in the alternative, from 0.001 to 0.05 wt %, or in the alternative, from 0.001 to 0.1 wt %, or in the alternative, from 0.005 to 0.1 wt %.

The disclosure further provides the process according to any embodiment disclosed herein except that the fuel source is selected from the group consisting of methane, hydrogen, ethane, ethylene, propane, propylene, coke and any combination of two or more thereof. In a certain embodiment, the fuel source comprises coke which is in the form of residue on used catalyst particles. In a particular embodiment, the fuel source comprises methane. In yet another embodiment, the fuel source comprises coke. In yet another embodiment, the fuel source comprises methane and coke.

In another embodiment, the disclosure provides the process to react an oxygen containing regenerated catalyst stream according to any embodiment disclosed herein except that the fuel source comprises methane and the combined regenerated catalyst stream and methane comprises at least 0.001 wt % methane.

In another embodiment, the disclosure provides the process to react an oxygen containing regenerated catalyst stream according to any embodiment disclosed herein except that the fuel source comprises used catalyst which comprises coke residue and the combined regenerated catalyst stream and used catalyst comprises at least 0.001 wt % coke residue.

In another embodiment, the disclosure provides the process to react an oxygen containing regenerated catalyst stream according to any embodiment disclosed herein except that the regenerated catalyst stream and vapor fuel source are reacted at a temperature from 550° C. to 750° C. All individual values and subranges from 550° C. to 750° C. are included and disclosed herein; for example, the reaction temperature may be from a lower limit of 550, 600, 650, or 700° C. to an upper limit of 575, 625, 675, 725 or 750° C. For example, the reaction temperature may range from 550° C. to 750° C., or in the alternative, from 550° C. to 650° C., or in the alternative, from 650° C. to 750° C., or in the alternative, from 580° C. to 690° C., or in the alternative, from 620° C. to 680° C.

In another embodiment, the disclosure provides the process to react an oxygen containing regenerated catalyst stream according to any embodiment disclosed herein except that the regenerated catalyst stream and a vapor fuel source are contacted for a time of at least 0.2 seconds prior to the step of injecting the usable regenerated catalyst stream into the hydrocarbon fluidized bed reactor. All individual values and subranges from at least 0.2 seconds are disclosed and included herein; for example, the reaction time can be from a lower limit of, 0.2, 0.4, 0.6, 0.8, 1.0, 1.2, 1.4 or 1.6 seconds. In a particular embodiment, the reaction time for the regenerated catalyst stream and the vapor fuel source may be from an upper limit of 10 seconds. All individual values and subranges from no more than 10 seconds are included and disclosed herein. For example, reaction time may be from an upper limit of 10, 8, 6, 4, 2, or 0.5 seconds. For example, the reaction time for the regenerated catalyst stream and the vapor fuel source may be from 0.40 to 2.00 seconds, or in the alternative, from 0.40 to 1.20 seconds, or in the alternative, from 1.20 to 2.00 seconds, or in the alternative, from 0.40 to 1.60 seconds, or in the alternative, from 0.70 to 2.00 seconds.

Exemplary vapor fuel sources include ethane, methane, ethylene, propane, propylene, hydrogen, and any combination of two or more thereof.

In another embodiment, the disclosure provides the process to react an oxygen containing regenerated catalyst stream according to any embodiment disclosed herein except that the regenerated catalyst stream and solid fuel source are reacted at a temperature from 400° C. to 700° C. prior to the step of injecting the usable regenerated catalyst stream into the hydrocarbon fluidized bed reactor. All individual values and subranges from 400° C. to 700° C. are included and disclosed herein; for example, the reaction temperature may be from a lower limit of 400, 450, 500, 550, 600, or 650° C. to an upper limit of 425, 475, 525, 575, 625, 675, or 700° C. For example, the reaction temperature for the reaction between the regenerated catalyst stream and the solid fuel source may range from 400° C. to 700° C., or in the alternative, from 400° C. to 550° C., or in the alternative, from 550° C. to 700° C., or in the alternative, from 480° C. to 600° C., or in the alternative, from 500° C. to 630° C.

In another embodiment, the disclosure provides the process to react an oxygen containing regenerated catalyst stream according to any embodiment disclosed herein except that the regenerated catalyst stream and a solid fuel source are reacted for a reaction time of at least 0.1 seconds prior to the step of injecting the usable regenerated catalyst stream into the hydrocarbon fluidized bed reactor. All individual values and subranges from at least 0.1 seconds are disclosed and included herein; for example, the reaction time can be from a lower limit of 0.1, 0.20, 2.0, 20 or 40 seconds. In a particular embodiment, the reaction time for the regenerated catalyst stream and the vapor fuel source may be from an upper limit of 60 seconds. All individual values and subranges from no more than 60 seconds are included and disclosed herein. For example, reaction time may be from an upper limit of 60, 55, 45, 25, 2, or 0.2 seconds. For example, the reaction time for the regenerated catalyst stream and the vapor fuel source may be from 0.1 to 60 seconds, or in the alternative, from 0.1 to 40 seconds, or in the alternative, from 20 to 60 seconds, or in the alternative, from 0.10 to 10 seconds, or in the alternative, from 0.1 to 20 seconds.

Exemplary solid fuel sources include coke, coke residue on used catalyst.

The process of the present disclosure may be used in conjunction with a process for the dehydrogenation of at least one and preferably both of: 1) a paraffinic hydrocarbon compounds, preferably a lower alkane having from 2 to 6 carbon atoms but more preferably less than 5 carbon atoms, for example ethane, propane, isobutane and n-butane, to the corresponding olefin, namely, ethylene, propylene, isobutylene and n-butylene, respectively, and 2) an alkylaromatic hydrocarbon compound, preferably a lower alkylaromatic hydrocarbon compound, such as for example, ethylbenzene, propylbenzene, isopropyl benzene, and methyl ethylbenzene, to the corresponding vinyl aromatic hydrocarbon compound, (that is "alkenylaromatic"), namely, styrene, cumene or alpha-methyl styrene. Several embodiments of the present invention are described including both the simultaneous and separate dehydrogenation of lower alkanes and alkylaromatics. The invention is useful to prepare styrene and ethylene from ethylbenzene and ethane, respectively. Likewise, cumene and propylene can be prepared from propylbenzene and propane, respectively.

The types and conditions of a hydrocarbon dehydrogenation reactor are disclosed, for example, in WO 2005/077867 and PCT/US16/21127, the disclosures of which are incorporated herein in their entireties.

The dehydrogenation reactor product mixture and fluidized catalyst rise in the reactor cylinder. At the top of the riser reactor, the used catalyst and hydrocarbon product are separated. The used catalyst settles in an annular space between the outside wall of the riser tube and an inner wall of the reactor housing. The used catalyst is then generally sent to a regenerator/reactivator in which the catalyst is contacted with a regeneration fluid, usually an oxygen-containing gas and a supplemental fuel for combustion of any remaining hydrocarbons and to heat the catalyst, and the regenerated catalyst is sent back to the dehydrogenation reactor. Used catalyst may also be recycled to the reactor without regeneration.

Referring to FIG. 1 an on-purpose catalytic dehydrogenation system 1, for example, for production of propylene, is shown. Catalytic dehydrogenation system 1 includes a catalytic dehydrogenation reactor 10 into which one or more hydrocarbon feeds are injected through feed line 15. Regenerated catalyst may be fed through line 20 first into line 25 from which it is then passed into fluidized bed dehydrogenation reactor 10. A product stream exits reactor 10 passing into a catalyst separation zone 30 in which the fluidized catalyst particles are separated from the gaseous components of the product stream. In the embodiment shown in FIG. 1, the catalyst separation zone 30 comprises a plurality of cyclone separators 35, each terminating in a dipleg 40, which empties into a stripping section 45. Fluidization gas enters the reactor recycle catalyst fluidization/stripping section 45 through feed line 75 which distributes fluidization gas over the entire annular cross section in a distributor commonly used in fluidized applications.

In stripping internals section 45, the catalyst particles may soak in a fluidization gas which comprises methane, natural gas, ethane, hydrogen, nitrogen, steam or any combination thereof. Such fluidization is disclosed in U.S. Patent Application No. 62/333,313, the disclosure of which is incorporated herein in its entirety. In this embodiment, methane may optionally enter the stripping internals section 45 through feed line 75 into a standard fluidized bed distributor which will evenly distribute the gas across the annular cross section. Alternatively, a portion of the separated catalyst particles may enter used catalyst feed line 55 and be passed into the catalyst regenerator system 60. In one embodiment of the inventive process, some of the used catalyst stream, which optionally includes methane, is passed into line 25 wherein it passes to oxygen reaction zone 65 wherein it contacts the regenerated catalyst stream. The oxygen reaction zone 65 is temperature controlled by controlling the amount of regenerated catalyst and recycled used catalyst such that the reaction between the oxygen and coke residue present on the used catalyst and/or methane and/or other fuel occurs. The reaction product of this reaction is then passed back into the dehydrogenation reactor 10. The reaction which occurs in oxygen reaction zone 65 reduces the amount of oxygen which enters into the dehydrogenation reactor 10. In a particular embodiment, no nitrogen is used to strip oxygen from the regenerated catalyst stream.

EXAMPLES

The following examples illustrate the present invention but are not intended to limit the scope of the invention.

Inventive Example 1

Methane as a Fuel Source

The data in Table 1 was collected on a vertical 36-inch quartz glass reactor with an internal diameter of 1.5 inches. The reactor was loaded with 50 grams of dehydrogenation catalyst, having the following composition: In preferred embodiments, the catalyst comprises from 0.1 to 34 wt %, preferably 0.2 to 3.8 wt %, gallium oxide ($Ga_2O_3$); from 1 to 300 parts per million (ppm), preferably 50 to 300 ppm, by weight platinum; from 0 to 5 wt %, preferably 0.01 to 1 wt %, of an alkaline and/or earth-alkaline such as potassium; from 0.08 to 3 wt % silica; and the balance to 100 wt % being alumina, which resulted on a catalyst bed height of 2.2 inches. The inlet gas was introduced at the bottom of the reactor and a quartz frit was used to distribute the gas flow across the reactor diameter. The volumetric flow of the inlet gas was 1100 standard cubic centimeters per minute. The inlet gas flow caused the catalyst to fluidize. The inlet gas composition was 9.6% $O_2$, 1.6% He, 0.5-2% methane and the balance to 100% nitrogen. The combustion of methane with oxygen was measured between 475 and 700° C. and a pressure of 2 psig. The information in Table 2 is derived from the data in Table 1, specifically, a conversion at each temperature is calculated at the gas residence time in fluidized bed of 50 grams of catalyst at 1.3 seconds. The conversion is then adjusted to 100% and a new required residence time is calculated at the target temperature assuming a bubbling bed density of 66 lb/ft³ and an operating plant density of 55 lb/ft³ of catalyst in the reactor.

TABLE 1

| Temperature ° C. | Methane Conversion (%) |
|---|---|
| 500 | 13 |
| 550 | 30 |
| 600 | 60 |
| 650 | 80 |
| 700 | 100 |

TABLE 2

| Temperature ° C. | Vapor Fuel Residence Time required for ~100% conversion of Methane Seconds |
|---|---|
| 500 | 9.9 |
| 550 | 4.3 |
| 600 | 2.1 |
| 650 | 1.6 |
| 700 | 1.3 |

Inventive Example 2

Catalyst Coke Residue as a Fuel

Tests were carried out in a thermogravimetric analyzer to determine the combustion rate of coke on the catalyst, as described above. A catalyst with coke was heated up in argon to the target temperature. When the target temperature was achieved, air was fed to the unit and the mass rate of change was measured. The resulting data are shown in Table 3. The catalyst with coke was prepared under the following conditions: in the reactor as described above, 1 g of catalyst with no diluent was loaded in the reactor and topped off reactor with 2 mm×2 mm quartz stock and the reactor run for 1 hour at 700° C.; Propane flow of 46.24 sccm; Nitrogen flow of 5.14 sccm; and WHSV of 5 l/hr.

TABLE 3

| Temperature, ° C. | Coke Combustion Rate, lb $O_2$/sec/lb catalyst |
|---|---|
| 500 | 0.0001 |
| 600 | 0.0017 |
| 700 | 0.0020 |

In order to calculate the required time to burn the oxygen out of the regenerated catalyst stream, the following example is presented. If 100 lb/hr of oxygen is fed with 500,000 lb/hr of regenerated catalyst and 500,000 lb/hr of catalyst recycled from the reactor stripper. Since the recycle catalyst is the only catalyst with fuel, the following table describes how many seconds it would take to remove the oxygen. The resulting data are shown in Table 4.

TABLE 4

| Temperature, ° C. | Coke Combustion Rate, lb $O_2$/sec/lb catalyst | Oxygen Burn Rate, lb $O_2$/sec | Time Required, seconds |
|---|---|---|---|
| 500 | 0.0001 | 50 | 2 |
| 600 | 0.0017 | 850 | 0.12 |
| 700 | 0.0020 | 1000 | 0.10 |

The present invention may be embodied in other forms without departing from the spirit and the essential attributes thereof, and, accordingly, reference should be made to the appended claims, rather than to the foregoing specification, as indicating the scope of the invention.

The invention claimed is:

1. A process to react an oxygen containing regenerated catalyst stream prior to use in a fluidized bed reactor comprising:
    regenerating a used catalyst stream to produce a regenerated catalyst stream comprising a regenerated catalyst and at least 0.001 wt % oxygen;
    reacting the regenerated catalyst stream with a fuel source at a temperature of from at least 400° C. and a reaction time of from 0.1 to 60 seconds thereby forming oxides and reducing the amount of oxygen in the regenerated catalyst stream to produce an oxygen-minimized regenerated catalyst stream; and injecting the oxygen-minimized regenerated catalyst stream into a hydrocarbon fluidized bed reactor.

2. The process to react an oxygen containing regenerated catalyst stream according to claim 1, wherein the fuel source comprises at least 0.001 wt % methane based on the combined weight of the regenerated catalyst stream and the fuel source.

3. The process to react an oxygen containing regenerated catalyst stream according to claim 1, wherein the fuel source comprises at least 0.001 wt % coke residue based on the combined weight of the regenerated catalyst stream and the fuel source.

4. The process to react an oxygen containing regenerated catalyst stream according to claim 1, wherein the fuel source comprises a vapor fuel.

5. The process to react an oxygen containing regenerated catalyst stream according to claim 4, wherein reacting the regenerated catalyst stream with the vapor fuel source is at a temperature of from 550° C. to 750° C.

6. The process to react an oxygen containing regenerated catalyst stream according to claim 1, wherein the fuel source comprises a solid fuel and wherein reacting the regenerated catalyst stream with the solid fuel source is at a temperature of from 400° C. to 700° C.

7. The process to react an oxygen containing regenerated catalyst stream according to claim 1, wherein the fuel source comprises hydrogen.

8. A process to react an oxygen containing regenerated catalyst stream prior to use in a fluidized bed reactor comprising:

regenerating a used catalyst stream to produce a regenerated catalyst stream comprising a regenerated catalyst and at least 0.001 wt % oxygen;

reacting the regenerated catalyst stream with a solid fuel source at a temperature of from at least 400° C. and a reaction time of from 0.1 to 60 seconds thereby forming oxides and reducing the amount of oxygen in the regenerated catalyst stream to produce an oxygen-minimized regenerated catalyst stream; and injecting the oxygen-minimized regenerated catalyst stream into a hydrocarbon fluidized bed reactor.

9. The process to react an oxygen containing regenerated catalyst stream according to claim 8, wherein the solid fuel source comprises coke residue.

10. The process to react an oxygen containing regenerated catalyst stream according to claim 8, wherein reacting the regenerated catalyst stream with the solid fuel source is at a temperature of from 400° C. to 700° C.

11. The process to react an oxygen containing regenerated catalyst stream according to claim 9, wherein the fuel source comprises at least 0.001 wt % coke residue based on the combined weight of the regenerated catalyst stream and the solid fuel source.

12. The process to react an oxygen containing regenerated catalyst stream according to claim 8, wherein the regenerated catalyst stream is reacted with a combination of the solid fuel and a vapor fuel.

13. The process to react an oxygen containing regenerated catalyst stream according to claim 8, wherein the regenerated catalyst stream is reacted with a combination of the solid fuel and one or more of ethane, methane, ethylene, propane, propylene, hydrogen.

* * * * *

UNITED STATES PATENT AND TRADEMARK OFFICE
CERTIFICATE OF CORRECTION

PATENT NO. : 10,688,477 B2  
APPLICATION NO. : 16/094582  
DATED : June 23, 2020  
INVENTOR(S) : Matthew T. Pretz and Liwei Li Page 1 of 1

It is certified that error appears in the above-identified patent and that said Letters Patent is hereby corrected as shown below:

On the Title Page

Item (22) – PCT filed:
"May 5, 2017"

Should read:
--May 2, 2017--

Signed and Sealed this
Twenty-second Day of June, 2021

Drew Hirshfeld
*Performing the Functions and Duties of the*
*Under Secretary of Commerce for Intellectual Property and*
*Director of the United States Patent and Trademark Office*